United States Patent [19]

Hansen

[11] Patent Number: 5,030,826
[45] Date of Patent: Jul. 9, 1991

[54] SINGLE PORT THERMOSPRAY ION SOURCE WITH COAXIAL VAPOR FLOW

[75] Inventor: Stuart C. Hansen, Palo Alto, Calif.

[73] Assignee: Hewlett-Packard Company, Palo Alto, Calif.

[21] Appl. No.: 487,671

[22] Filed: Mar. 1, 1990

[51] Int. Cl.⁵ .................. B01D 59/44; H01J 49/00
[52] U.S. Cl. .................. 250/288; 250/281; 250/289
[58] Field of Search .......... 250/281, 282, 288, 288 A, 250/289

[56] References Cited

U.S. PATENT DOCUMENTS

| | | | |
|---|---|---|---|
| 4,647,772 | 3/1987 | Lewis et al. | 250/288 |
| 4,730,111 | 3/1988 | Vestal et al. | 250/288 |
| 4,794,252 | 12/1988 | Bateman et al. | 250/288 |
| 4,814,612 | 3/1989 | Vestal et al. | 250/288 |
| 4,851,700 | 7/1989 | Goodley | 250/288 A |
| 4,863,491 | 9/1989 | Brandt et al. | 250/288 A |

Primary Examiner—Bruce C. Anderson

[57] ABSTRACT

An apparatus for providing an ion vapor to be analyzed. A vaporizer probe, with a capillary tube extending into a vapor port of an ion source, has a release end which ejects a spray of vapor into a spray region of the ion source. Molecules of interest within the vapor may be ions pre-formed in solution or may be ionized by chemical ionization or plasma discharge ionization. A minor portion of the vapor is extracted from the spray chamber for mass analysis. The major portion is coaxially redirected from the spray chamber for return to the same port which receives the capillary tube of the vapor probe. A return tube is vacuum sealed to the port and is in fluid communication with a roughing pump which draws the ion vapor from the spray region through the ion source and the port for coaxial vapor backflow with the capillary tube. The ion source has a split-block structure for ease of both manufacture and routine maintenance.

19 Claims, 5 Drawing Sheets

SINGLE PORT THERMOSPRAY ION SOURCE WITH COAXIAL VAPOR FLOW

DESCRIPTION

1. Technical Field

The present invention relates generally to apparatus for interfacing liquid chromatography apparatus to mass spectrometers.

2. Background Art

Various systems are presently utilized in the analysis of solutions to provide molecular weight, isotope ratios, identification of functional groups, and elucidation of structure. Techniques used in combination with mass spectrometry include electrophoresis, gas chromatography and liquid chromatography.

In the use of a liquid chromatograph-mass spectrometer (LC/MS) system, it has been discovered that a thermospray technique extends the capability of LC/MS to ionize and produce identifying spectra for a broad range of thermally labile or nonvolatile compounds. The thermospray technique has been described in detail in U.S. Pat. Nos. 4,814,612 and 4,730,111 to Vestal et al. These patents teach the introduction of a fluid into a mass spectrometer ion source operating substantially below atmospheric pressure through a spray means which is typically heated so that the fluid emerges as a jet of fluid which is partially in the vapor phase. Classes of compounds that have been analyzed by thermo-spray LC/MS include underivatized amino acids, urea pesticides, peptides, vitamins, organic acids, and alkaloids.

The thermospray method is one in which a solution to be analyzed is introduced into a vaporizer probe having a heated capillary tube in which vaporization occurs. The release end of the capillary tube is extended into an ion source having a spray, or desolvation, chamber. The vapor from the capillary tube enters the spray chamber as a jet. The spray chamber is evacuated by use of a roughing vacuum pump to provide a pressure of between one and ten torr. A spray of evaporating droplets containing ions and molecules of analyte and solvent is formed in the chamber. A conical member having a hole at its apex is positioned to extend into the spray chamber so that ions exit the chamber into a high vacuum region for mass analysis. A typical pressure for the high vacuum region is $10^{-4}$ torr.

The vapor which is not extracted for mass analysis follows a linear path from the capillary tube which is received in an inlet port of the ion source, through the spray chamber of the ion source to exit from an outlet port of the ion source. This construction is shown and described in the above-cited patents to Vestal et al., as well as the thermospray apparatus of U.S. Pat. Nos. 4,794,252 to Bateman et al. and 4,647,772 to Lewis et al. In design and manufacture of these systems, a number of considerations are important. Firstly, the interfaces of the ion source with the roughing pump, with the mass spectrometer and with the capillary tube must all be vacuum sealed. Another consideration involves periodic cleaning of the various components of the system. The ion source in particular must be cleaned regularly. Consequently, the structure of the ion source and the interfacing of components should include features which both facilitate easy access and cleaning and minimize the risk of damage to other components as cleaning of a particular component takes place. Yet another consideration involves the trend in the electronics field to manufacture systems which are increasingly more compact.

It is an object of the present invention to provide an LC/MS system having features which facilitate vacuum sealing of components, maintenance of a clean system, and compactness.

DISCLOSURE OF THE INVENTION

The above object has been met by an apparatus for providing an ion vapor to be analyzed which includes a redirection of vapor spray residue to eliminate the need of an outlet port of an ion source. The redirection permits a more compact system since the connection to a roughing pump is no longer at that side of the ion source opposite the inlet. In actuality the inlet port serves the double function of acting as an outlet port.

The apparatus includes a vaporizer probe which heats a liquid sample to provide a vapor having molecules of interest. A capillary tube of the vaporizer probe has a release end which is received within the inlet port of the ion source. A vapor spray is ejected from the release end of the capillary tube into a spray chamber of the ion source. The ion source permits ionization of molecules by any of the methods of chemical ionization, discharge ionization or electron impact ionization, although electron impact is typically not used during the thermospray process.

Downstream of the release end of the vaporizer probe is an ion exit. A minor portion of the ion vapor exits the spray chamber through the ion exit which is in fluid communication with a high vacuum source. The major portion of the ion vapor continues past the ion exit into one of two identical return paths which are in fluid isolation other than at the inlets and outlets of the return paths. The return paths originate at the spray chamber and extend to the port which receives the capillary tube of the vaporizer probe. The single port of the ion source has a diameter which permits flow of the return vapor along the periphery of the vaporizer probe. A vacuum tube is sealed to the exterior of the ion source and is connected to a roughing pump. Flow to the pump is a coaxial flow with the vaporizer probe.

An advantage of the present invention is that a single port acts as both an inlet and an outlet for the ion source. In comparison to prior art thermospray systems, coupling of a vaporizer probe, an ion source and a roughing vacuum system is localized at the single port. Thus, the number of vacuum sealed couplings within the system is significantly reduced, thereby reducing the likelihood of vacuum system failure. Moreover, by redirecting the ion vapor to its origin, a more compact LC/MS system is possible.

Additional advantages of the present invention result from manufacturing the ion source in the form of a pair of metallic blocks. Each block includes a recessed region which provides one of the two return paths for the ion vapor to the port. The blocks have corresponding sequences of grooves of varying dimensions. The grooves define the spray chamber when the blocks are placed in abutting relation. During periodic maintenance, the blocks are separated, completely exposing the areas which are contacted by the vapor. In this manner, the ion source can be quickly and thoroughly cleaned. Moreover, the two-block structure of the ion source promotes ease of manufacture since the critical internal structure of the ion source is machined with the interior exposed. That is, the blocks are individually machined to produce the recessed regions and the grooves in contrast to conventional ion sources which require drilling to produce the internal bores.

Another advantage of the two-block structure is that the transition regions of the varying diameter grooves that form the spray chamber can be machined to form truncated spherical regions. It is thought that the smoother, more refined dimensional changes permit lower operating temperatures in the analysis of most compounds. Lower operating temperatures permit the ion source to be operated for a longer period of time between routine maintenance and also reduce thermal degradation of the analyte.

Yet another advantage of the single-port ion source is that it frees the ion source for connection of a second vacuum coupling port to conventional gas chromatography/mass spectrometry (GC/MS) interfaces. Use of the ion source with a system which permits both LC/MS and GC/MS analysis allows a saving in the time necessary to make the switch between the two technologies and also reduces the risk of equipment damage during the switch.

BEST MODE FOR CARRYING OUT THE INVENTION

Figure 1:
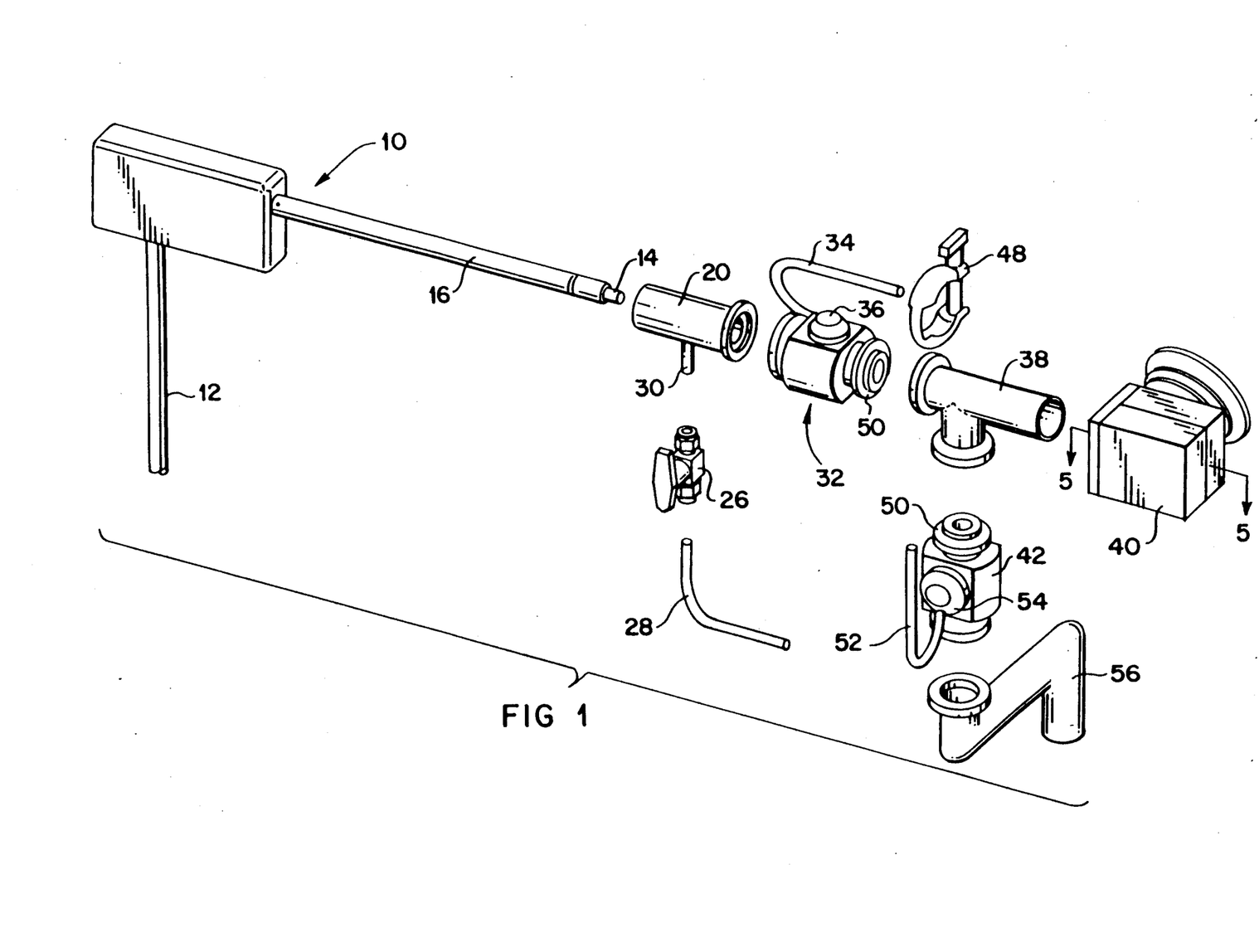
FIG. 1 is an exploded perspective view of a thermospray system in accord with the present invention.
Figure 2:
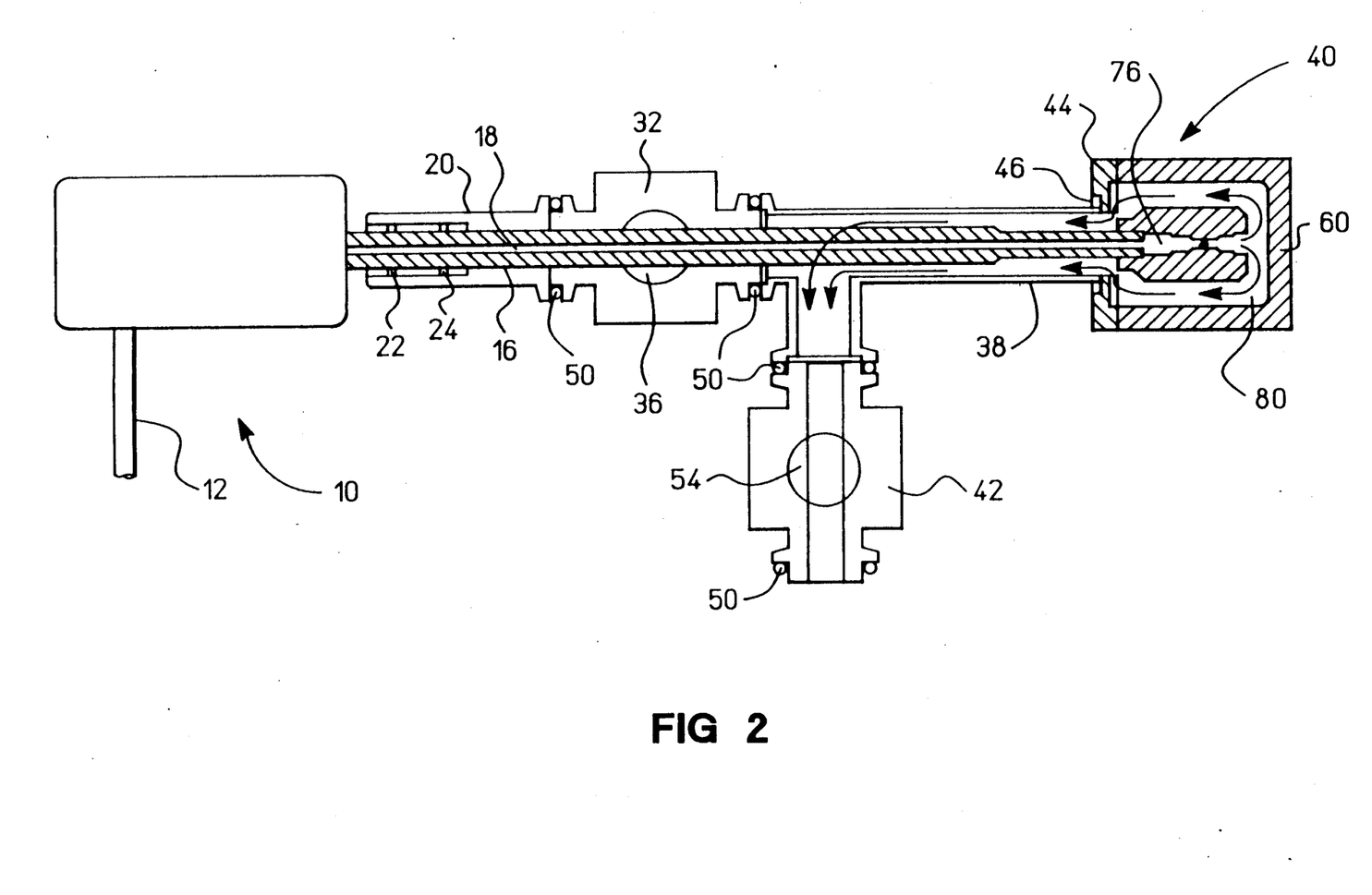
FIG. 2 is a schematical side view of the system of FIG. 1.

Referring to FIGS. 1 and 2, the thermospray system includes a vaporizer probe 10 which receives LC effluent through a tubing 12 and heats the effluent to provide a jet at a release end 14 of a capillary tube 16. The vaporizer probe is of the type described in U.S. Pat. No. 4,730,111 to Vestal et al. and may be purchased from Hewlett-Packard Co.

The capillary tube 16 of the vaporizer probe 10 has an axial passageway 18. The liquid effluent is pumped into the passageway and is heated to provide the desired degree of vaporization. The capillary tube passageway 18 typically has a diameter of 0.015 mm, but this is not critical. A conductive tubing surrounds the capillary tube and serves the function of providing heat along the length of the tube. An optimum temperature is one which provides 95% vaporization, since 100% vaporization may result in a high temperature runaway condition.

The capillary tube portion 16 of the vaporizer probe 10 extends through a vacuum lock 20. The vacuum lock houses a pair of circular seals. The circular seals are known in the art as K-F seals and vacuum seal the portion of the vaporizer probe towards the release end 14 after insertion into the sheath 20. Pressure within the sheath may be adjusted by operation of a valve member 26 which is in fluid communication with a vacuum tube 28 and an outlet 30 of the sheath.

From the sheath 20, the capillary tube portion 16 of the vaporizer probe 10 enters an isolation valve 32. The isolation valve includes a handle 34 which is fixed to a plug 36. When the plug is rotated in a first direction by manipulation of the handle 34, a bore through the plug is brought into alignment with an axial bore through the isolation valve 32. In this alignment, the capillary tube portion 16 may penetrate the isolation valve. Rotation of the plug 36 on its axis, however, vacuum seals one end of the isolation valve from the opposite end. Thus, during routine maintenance of the thermospray system, the vaporizer probe may be extracted until it no longer extends into the isolation valve but still has a portion which is surrounded by the circular seals 22 and 24 of the sheath 20. The plug 36 can then be rotated 90°, whereafter the vaporizer probe may be completely removed without venting the thermospray system downstream of the isolation valve. That is, the isolation valve allows the vaporizer probe to be cleaned, replaced or repaired without exposing the remainder of the system to the ambient atmosphere.

Attached to the isolation valve 32 is a return tube 38. The return tube has an asymmetrical T-shape which provides fluid communication between the isolation valve 32, an ion source 40 and a roughing pump isolation valve 42. The capillary tube portion 16 of the vaporizer probe 10 extends through the return tube for contact with the ion source. As will be explained more fully below, the vapor is projected into the ion source, whereafter the major portion of the vapor is redirected for exit from the ion source about the capillary tube portion. This flow is best seen in FIG. 2. The ion source is shown schematically in FIGS. 1 and 2, but will be explained more fully below with reference to FIGS. 3–5. The return tube 38 abuts a face plate 44 of the ion source 40. A multifunctional seal 46 provides gas-tight connection of the coaxial fluid return tube to the ion source and further provides electrical isolation of the vacuum system and the ion source.

A single clamp 48 is illustrated for connection of the isolation valves 32 and 42 with other components of the system. However, in practice the connections at both ends of the isolation valves are made using clamps such as 48, as well as a plurality of o-rings 50. The roughing pump isolation valve 42 operates in the same manner as the above-described isolation valve, having a handle 52 and a plug 54 which are rotated to selectively close fluid communication between the return tube 38 and a vacuum tube 56 which leads to a roughing pump, not shown.

Figure 3:
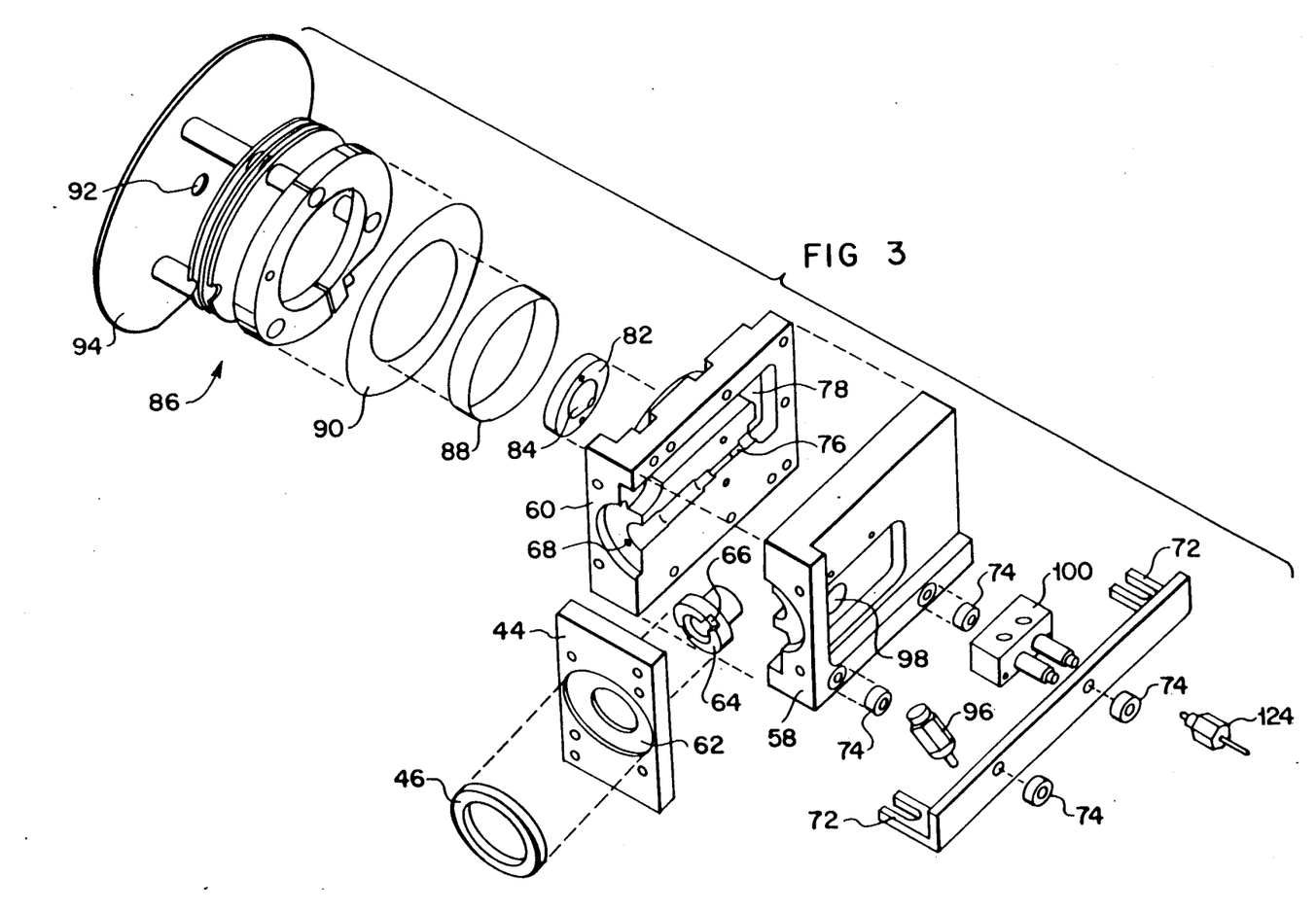
FIG. 3 is an exploded perspective view of the ion source of FIG. 2.

Referring to FIG. 3, the ion source 40 may be seen to include the face plate 44, a front block 58 and a rear block 60, all of which are connected together by conventional fastening hardware, not shown. The face plate 44 includes a recessed annular region 62 which receives the multifunctional seal 46 that provides the gastight electrically isolating connection of the ion source and the coaxial vapor flow system.

The vaporizer probe described above extends through the face plate 44 and is received within a vaporizer seal 64. The vaporizer seal isolates the flow into the ion source 40 from the flow exiting the ion source. The seal 64 is fixed to the front and rear blocks 58 and 60 by bolts which project through notched regions 66 of the seal into internally-threaded holes 68 in the blocks.

A mounting bar 70 having feet 72 is attached to the front block 58 by fastening hardware, not shown. Spacers 74 provide the proper alignment for attachment to a support structure.

The rear block 60 includes a plurality of grooves which define one half of an axial spray chamber 76. At the downstream end of the spray chamber is the inlet of a vapor return path 78 which proceeds upwardly and then forwardly for outlet at the face plate 44. The axial spray chamber 76 and the vapor return path 78 of the rear block 60 may be best seen in FIG. 2. This figure shows a second vapor return path 80 which proceeds downwardly and then forwardly from the downstream end of the spray chamber. In actuality, the second return path 80 is a recess within the front block 58 of FIG. 3. Thus, any upward flow of vapor from the spray chamber is through the rear block while any downward flow is through the front block.

An ion exit member 82 is fixed to the rear block 60 of the ion source 40. The ion exit member includes a frustroconically-shaped portion having a bore extending therethrough. The frustroconically-shaped portion projects slightly into the axial spray chamber 76 formed by the machining of corresponding grooves in the front and rear blocks 58 and 60. A minor portion of the vapor escapes through the ion exit member for mass analysis. As will be explained more fully below, the region which begins at the base of the frustroconically-shaped portion of the ion exit member is a high vacuum region. Within this high vacuum region is a conventional focus lens assembly 86. The focus lens assembly is electrically insulated from ion source block 60 by insulating elements 88 and 90. Ionized molecules of interest are directed by the components through an entrance aperture 92 of a plate 94 to pass into a mass spectrometer.

Ionization of the molecules of a sample can occur in more than one way. For example, the liquid sample which enters the vaporizer probe may contain ions which are not themselves of interest but which transfer ionization to molecules of interest by ion-molecule collision processes. This process is referred to as chemical ionization. For example, a liquid sample to be analyzed may be combined with a solution of ammonium acetate so that primary ions of $NH_4+$ and $CH_3COO-$ are formed in the spray. These ions can react with sample molecules forming $NH_4+$ or $CH_3COO-$ adducts, which are analyzed by the mass spectrometer.

A second method of ionization is plasma discharge ionization. As shown in FIG. 3, the ion source 40 includes a discharge electrode 96 having an end which enters into the axial spray chamber 76 at a 45° angle through an aperture 98 in the front block 58 of the ion source. A discharge is established between the electrode 96 and the wall of the spray chamber by maintaining a current of approximately 200 microamperes between the electrode and the wall. Neutral molecules in the thermospray enter the spray region and are ionized by collision with free electrons and other charged particles.

The ion source 40 includes a third means for causing ionization. A filament holder 100 secures a filament which is connected to a power supply for creating a current through the filament. A potential difference of 1000 volts is typical. The filament emits electrons through thermal emission and the electrons impact solvent and analyte molecules in the vapor phase. By virtue of chemical ionization, positive or negative ions are created. Direct electron impact ionization is typically not used in thermo-spray technology. However, it has been discovered that electron impact is particularly useful for diagnostic purposes. Current is initiated through the filament and in the absence of LC liquid within the spray chamber the gases within the chamber are directly ionized. The ionized gases are analyzed to determine the particular ions that are characteristic of the resident gases. This information is helpful in tuning of the system.

Figure 4:
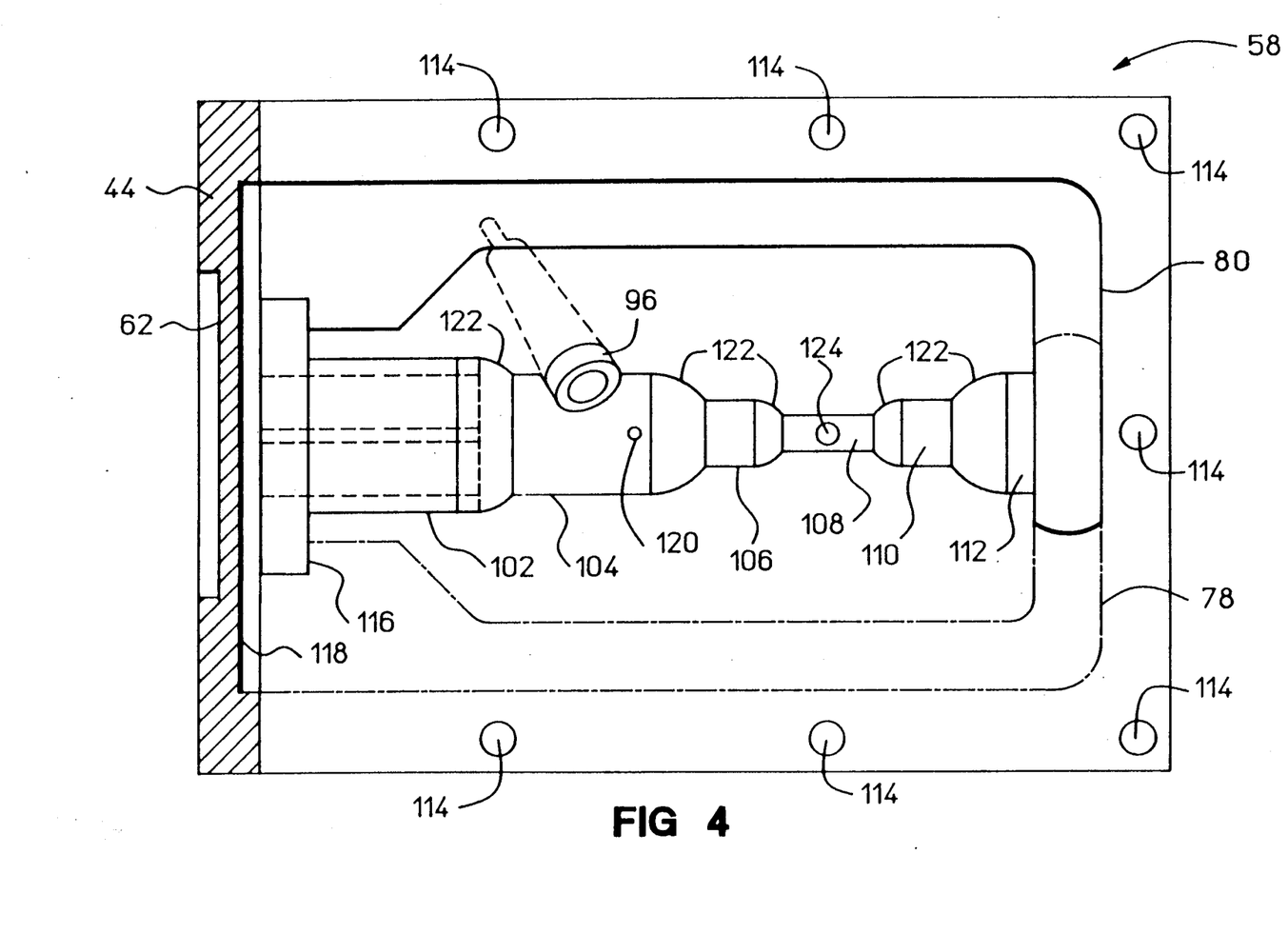
FIG. 4 is a side view of a front block of the ion source of FIG. 3.

Referring now to FIG. 4, the front block 58 of the ion source is shown as having been rotated 180° from top to bottom relative to the orientation of FIG. 3. The front block 58 includes a Venturi-like flow path comprising a plurality of grooves 102, 104, 106, 108, 110 and 112. Each groove 102-112 of the front block is identical to a groove in the rear block of the ion source so that as the blocks are placed in abutting relation, the axial spray chamber described above is formed. The blocks are secured together by fastening hardware which penetrate bores 114 along the outside of the blocks.

Figure 5:
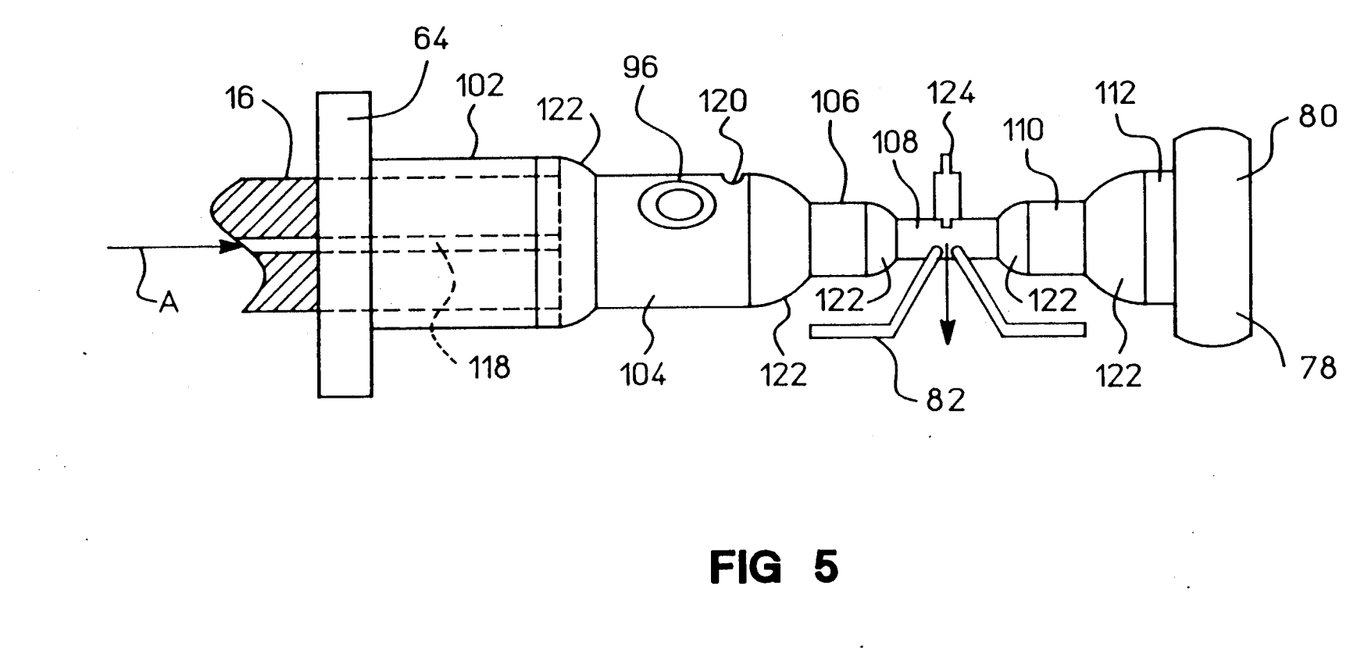
FIG. 5 is a schematic view of the spray chamber of the ion source of FIG. 3.

Referring now to FIGS. 4 and 5, vapor enters the Venturi-like spray chamber through the capillary tube of the vaporizer probe, as indicated by arrow A. The release end of the capillary tube is secured within the vaporizer seal 64 which is mounted to the blocks 58 and 60 that form the ion source. As shown in FIG. 4, the front block 58 has a relief 116 which receives the vaporizer seal. The face plate 44 is fixed to the front block by fastening hardware. The recessed annular region 62 has an outside diameter corresponding to the multi-functional seal described above for sealing the return tube that houses the capillary tube prior to entrance into the ion source. The side of the face plate 44 opposite the recessed annular region 62 also include a cutaway axial region 118.

In operation, vapor exits from the capillary tube 16 into grooves 104 of the front and rear blocks which define one portion of the ion source spray chamber, as shown in FIGS. 4 and 5. By use of pre-formed ions in solution, the vapor may already include ions. Alternatively, ionization may take place by means of the discharge electrode 96. The discharge electrode is secured within an internally-threaded bore of the front block 58. Also within that portion of the spray chamber defined by the grooves 104 is a 0.5 mm electron-entrance bore 120 which may be employed for electron impact chemical ionization.

The now-ionized vapor is compressed by entrance into the portion of the spray chamber defined by grooves 106. Because the spray chamber of the present invention is formed by the machining of grooves into two separate blocks, the transitions 122 from one groove 102-112 to an adjacent groove may be formed by rounded end mills to provide smooth radius transitions. That is, the transitions 122 may each have a truncated spherical configuration. This is not practical where an axial spray chamber is formed by blunt drills and mills. It is believed that the smooth radius transitions at internal bore variations permit operating temperatures that may be as much as 100° C. below the operating temperatures of prior art sources in the analysis of most compounds. The reduced operating temperatures reduces thermal degradation of the analyte and permits users to extend the periods between routine cleanings of the ion source.

From the portion of the spray chamber defined by grooves 106, the vapor is again compressed as the ion vapor enters grooves 108. The ion exit member 82 projects into the spray chamber to permit extraction of a minor portion of the ion vapor for mass analysis. Typically, the ion exit member projects into the ion chamber to a position just short of the center. Opposite the ion exit member 82 is a fragmenter electrode 124. The function of the fragmenter electrode is described in detail in U.S. Pat. No. 4,647,772 to Lewis et al. Briefly, the electrode is capable of generating an electrostatic field capable of retarding and deflecting ions into the aperture of the ion exit member 82. A typical pressure within the spray chamber is 10 torr, while the pressure on the backside of the ion exit member is a high vacuum pressure, e.g., $10^{-4}$ torr.

The major portion of the vapor then travels through the grooves 110 and 112 into the vapor return paths of the front and rear blocks. As best seen in FIG. 4, the vapor return path 80 of the front block 58 is through only one half of the block. Vapor progresses from the ion chamber, through the vapor return path 80 and enters into the cutaway axial region 118 at the back of the face plate 44. The vapor then exits through the center of the face plate. A corresponding vapor return path 78 is defined by a recessed region in the rear block. Each of the vapor return paths 78 and 80 is defined by a recess in one block and by the planar surface of the other block. Thus, the schematic view of FIG. 2 should not be read as illustrating an ion source in which a cross section may be taken to intersect both of the vapor return paths 78 and 80. The two-block structure of the ion source promotes ease of manufacture and facilitates periodic cleaning.

Both of the vapor return paths 78 and 80 outlet at the port of the ion source which receives the capillary tube 16. Thus, the single port acts as both an inlet and an outlet. This minimizes the number of vacuum sealed couplings within the system. The redirection of vapor through the port has the further advantage of providing a more compact system than LC/MS systems in which vapor is projected into one end of an ion source and is evacuated from the end distant the entrance end.

I claim:

1. An apparatus for providing an ion vapor to be analyzed comprising,
    means for vaporizing a sample liquid and for directing vaporized sample in a first direction,
    means in communication with said vaporizing means for receiving the vaporized sample and for ionizing molecules of said vaporized sample to create an ion vapor flow in said first direction,
    means downstream of said ionizing means for extracting a minor portion of said ion vapor flow for mass analysis, and
    path means downstream of said extracting means for preventing flow in said first direction and for redirecting the remaining major portion of said ion vapor flow along a second direction generally opposite to said first direction.

2. The apparatus of claim 1 wherein said ionizing means includes an ion source having a receptor region situated to receive said vaporized sample, said path means including an internal pathway through said receptor region and then folded about the receptor region in a configuration to direct said major ion vapor flow in said second direction.

3. The portion of said apparatus of claim 2 wherein said ion source has a vapor port and wherein said vaporizing means includes a capillary tube projecting through said vapor port and aligned to eject said vaporized sample into an upstream end of said receptor region, said internal pathway of said ion source having an outlet end at said vapor port for return flow through said vapor port about said capillary tube.

4. The apparatus of claim 3 wherein said path means further includes a return tube coaxial with said capillary tube, said return tube being in fluid communication with said internal pathway at said vapor port.

5. The apparatus of claim 1 wherein said ionizing means includes a discharge electrode.

6. An ion source comprising,
    a housing having a sample vapor port and having a vapor spray chamber in communication with said sample vapor port to receive a vapor flow via said vapor port,
    means for ionizing molecules within said vapor spray chamber, and
    ion extraction means in communication with said spray chamber for receiving ions from said vapor spray chamber,
    said housing having an exhaust path defined therein, said exhaust path having an inlet downstream of said ion extraction means and further having an outlet to said sample vapor port, said housing being sealed opposite to said vapor port.

7. The ion source of claim 6 wherein said housing includes first and second split blocks configured to define said vapor spray chamber and said exhaust path when in abutting relation.

8. The ion source of claim 7 wherein each of said blocks includes a recessed region and wherein said exhaust path is a first exhaust path, said recessed region of said first block defining said first exhaust path, said recessed region of said second block defining a second exhaust path, said exhaust paths being in fluid isolation other than at opposed ends thereof.

9. The ion source of claim 7 wherein each block has a corresponding sequence of grooves of varying dimensions, said grooves defining said spray chamber when said blocks are in said abutting relation.

10. The ion source of claim 9 wherein said ion extraction means includes a hollow conical member having an aperture at the apex, said aperture being in fluid communication with one of said grooves of said first block.

11. The ion source of claim 9 wherein said grooves are joined by truncated spherical regions.

12. The ion source of claim 6 further comprising a tube having a diameter to allow axial insertion of a capillary tube of the type for injecting vapor into said spray chamber via said sample vapor port and to further allow coaxial return flow of vapor from said exhaust path.

13. An apparatus for providing an ion vapor to be analyzed comprising,
    means for vaporizing a liquid sample, said vaporizing means having a tubular outlet portion,
    an ion source having a port and means for seating said outlet portion of said vaporizing means to said ion source via said port, the area of said port being greater than the cross-sectional area of said tubular outlet portion, said ion source further having a spray region at a release end of said tubular outlet portion and having a vapor return path originating at said spray region opposite to said release end and extending to said port adjacent to said tubular outlet portion for flow thereabout, said ion source being sealed opposite to said port,
    an exhaust tube disposed in substantially coaxial alignment with said tubular outlet portion and coupled to said port,
    first vacuum means in fluid communication with said exhaust tube for drawing vapor from said spray chamber through said vapor return path and said port to provide a coaxial relationship of vapor flow.

through said tube with said outlet portion of said vaporizing means, and second vacuum means for drawing a minor portion of vapor from said spray region for mass analysis.

14. The apparatus of claim 13 wherein said vaporizing means includes a capillary tube.

15. The apparatus of claim 13 wherein said ion source includes first and second blocks, said first block having recessed regions defining said vapor return path, said second block having recessed regions defining a second vapor return path, said blocks having generally matching grooves defining said spray region when placed in abutting relation.

16. The apparatus of claim 13 further comprising means for ionizing molecules within said spray region.

17. The apparatus of claim 16 wherein said ionizing means is a means for ionizing by discharge and by electron impact.

18. The apparatus of claim 13 further comprising a valve member disposed between said tube and said first vacuum means to selectively seal said ion source from said first vacuum means.

19. The apparatus of claim 13 wherein said second vacuum means includes a hollow conical member having an aperture at the apex, said apex extending into said spray region.

* * * * *